United States Patent [19]

Scherkenbeck et al.

[11] Patent Number: 5,571,793
[45] Date of Patent: Nov. 5, 1996

[54] ENDOPARASITICIDAL COMPOSITIONS BASED ON OPEN-CHAIN TETRADEPSIPEPTIDES

[75] Inventors: Jürgen Scherkenbeck, Wermelskirchen; Peter Jeschke, Leverkusen; Andrew Plant, Odenthal; Achim Harder, Köln; Norbert Mencke, Leverkusen, all of Germany

[73] Assignee: Bayer Aktiengesellschaft, Leverkusen, Germany

[21] Appl. No.: 348,420

[22] Filed: Dec. 2, 1994

[30] Foreign Application Priority Data

Dec. 9, 1993 [DE] Germany .................... 43 41 992.5

[51] Int. Cl.$^6$ .......................... A61K 38/15; C07K 11/00
[52] U.S. Cl. .................. 514/19; 514/18; 514/20; 530/323
[58] Field of Search ................... 514/18, 19, 20; 530/323, 330, 332

[56] References Cited

FOREIGN PATENT DOCUMENTS

| | | |
|---|---|---|
| 0626376 | 11/1994 | European Pat. Off. . |
| 0626375 | 11/1994 | European Pat. Off. . |
| 4317458 | 12/1993 | Germany . |

OTHER PUBLICATIONS

Tetrahedron Letters, No. 46, issued 1977, Kanaoka et al, "Synthsis of Bassianolide", pp. 4049–4050.

Chemical Abstracts vol. 122, 1995, Abstract No. 133864.

Chemical Abstracts vol. 121, 1994, Astract No. 206,025.

H. G. Lerchen & H. Kunz: Tetrahedron Lett. 26 (43) pp. 5257–5260 (1985).

H. G. Lerchen & H. Kunz: Tetrahedron Lett. 28 (17) pp. 1873–1876 (1987).

B. F. Gisin: Helv. Chim. Acta 56 pp. 1476–1482 (1973).

R. Bowman et al: J. Chem. Soc. pp. 1346–1349 (1950).

J. R. McDermott et al: Can. J. Chem. 51 pp. 1915–1919 (1973).

E. Wurziger et al: Kontake [Catalysts] (Merck Darmstadt) 3 pp. 8–11 (1987).

S. M. Birnbaum et al: J. Amer. Chem. Soc. pp. 6054–6058 (1954).

C. S. Rondestvedt et al: Org. Reactions 11 pp. 189–260 (1960).

*Primary Examiner*—Jeffrey E. Russel
*Attorney, Agent, or Firm*—Sprung Horn Kramer & Woods

[57] ABSTRACT

The present invention relates to the use of open-chain tetradepsipepties of the formula

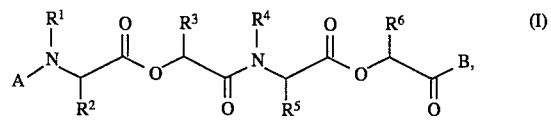

in a method for combatting endoparasites in humans and animals.

10 Claims, No Drawings

ENDOPARASITICIDAL COMPOSITIONS BASED ON OPEN-CHAIN TETRADEPSIPEPTIDES

The present invention relates to the use of open-chain tetradepsipeptides for combating endoparasites.

Open-chain tetradepsipeptides as starting substances for endoparasiticidally active cyclic depsipeptides having 28 ring atoms are the subject-matter of earlier, but not prior-published patent applications (German Patent Application P 43 17 457.4; P 43 17 432.9; P 43 17 458.2).

Nothing is known about a use of these compounds against endoparasites.

It has now been found that the open-chain tetradepsipeptides of the general formula (I)

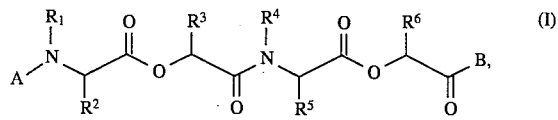

in which

A represents hydrogen, alkyl, aralkyl or an acyl radical, in particular of the formula —CO—$R^9$, in which $R^9$ represents straight-chain or branched alkyl, alkoxy, aralkyl or aralkoxy having up to 6 C atoms in the alkyl moiety, $R^1$ and $R^4$ independently of one another represent hydrogen, $C_1$–$C_8$-alkyl, $C_3$–$C_6$-cycloalkyl or aralkyl, $R^2$ and $R^5$ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which can optionally be substituted by one or two benzyloxycarbonyl radicals or by one, two, three or four alkyl radicals, or represent alkoxycarbonylaminoalkyl, 9-fluorenylmethoxycarbonyl(Fmoc)aminoalkyl, alkenyl, cycloalkyl, cycloalkylalkyl and optionally substituted aryl, arylalkyl or hetarylmethyl, substituents which may be mentioned being halogen, hydroxyl, alkyl, alkoxy, nitro or a radical $NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which can optionally also be interrupted by O, S and N and which is optionally substituted by $C_1$–$C_4$-alkyl, $R^3$ and $R^6$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl and optionally substituted aryl, arylalkyl or hetarylmethyl, substituents which may be mentioned being halogen, hydroxyl, alkyl, alkoxy, nitro or a radical $NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which can optionally also be interrupted by O, S and N and which is optionally substituted by $C_1$–$C_4$-alkyl, B represents hydroxyl, alkoxy having up to 4 carbon atoms or the radical $NR^7R^8$, in which $R^7$ and $R^8$ represent hydrogen, alkyl, aralkyl or aryl, and their optical isomers and racemates can be used in medicine and veterinary medicine for combating endoparasites.

Formula (I) provides a general definition of the open-chain tetradepsipeptides to be used according to the invention. Compounds of the formula (I) which are preferably used according to the invention are those in which A represents hydrogen or $C_{1-4}$-alkyl or benzyl, or represents a group of the formula —CO—$R^9$, in which $R^9$ represents straight-chain or branched $C_{1-4}$-alkyl, $C_{2-4}$-alkenyl, $C_{1-4}$-alkoxy or phenyl-alkoxy having up to 6 carbon atoms in the alkyl moiety, in particular tert-butoxy, benzyloxy, ethoxy, allyloxy, fluorenyl-9-methoxy or methoxy $R^1$ and $R^4$ independently of one another represent hydrogen, $C_{1-6}$-alkyl, $C_{3-6}$-cycloalkyl, phenyl-$C_{1-4}$-alkyl, $R^2$ and $R^5$ independently of one another represent hydrogen, straight-chain or branched $C_{1-8}$-alkyl, in particular methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_4$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyl-oxy-ethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_4$-alkylsulphinyl-$C_1$–$C_6$-alkyl, methylsulphinylethyl, $C_1$–$C_4$-alkyl-sulphonyl-$C_1$–$C_6$-alkyl, in particular methylsulphonylethyl, carboxy-$C_1$–$C_6$-alkyl, in particular carboxymethyl, carboxyethyl, $C_1$–$C_4$-alkoxycarbonyl-$C_1$–$C_6$- alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, guanido-$C_1$–$C_6$-alkyl, in particular guanidopropyl, $C_1$–$C_4$-alko- xycarbonylamino-$C_1$–$C_6$-alkyl, in particular tert-butoxycarbonylaminopropyl, tert-butoxycarbonylamino-butyl, 9-fluorenylmethoxycarbonyl (Fmoc)aminopropyl, 9-fluorenylmethoxycarbonyl (Fmoc)aminobutyl, $C_2$–$C_8$-alkenyl, in particular vinyl, allyl, butenyl $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, aryl, phenyl-$C_1$–$C_4$-alkyl, in particular phenylmethyl which can optionally be substituted by radicals from the series comprising halogen, in particular fluorine, chlorine, bromine or iodine, hydroxyl, $C_1$–$C_4$-alkoxy, in particular methoxy or ethoxy, $C_1$–$C_4$-alkyl, in particular methyl, nitro or a radical —$NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which is optionally substituted by $C_1$–$C_4$-alkyl, or represent hetarylmethyl, in particular benzo[b]thien-2-yl-methyl, benzo[b]thien-3-yl-methyl, naphth-1-yl-methyl, naphth-2-yl-methyl, pyrid-2-yl-methyl, pyrid-3-yl-methyl, fur-2-yl-methyl, fur-3-yl-methyl, indol-3-yl-methyl, N-methyl-indol-3-yl-methyl, imidazol-4-yl-methyl, N-methyl-imidazol-4-yl-methyl, $R^3$ and $R^6$ independently of one another represent hydrogen, straight-chain or branched $C_1$–$C_8$-alkyl, in particular methyl, ethyl, propyl, isopropyl, butyl, isobutyl, sec-butyl, pentyl, tert-butyl, pentyl, isopentyl, sec-pentyl, hexyl, isohexyl, sec-hexyl, heptyl, iso-heptyl, sec-heptyl, tert-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxy-ethyl, $C_1$–$C_6$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyl-oxyethyl, mercapto-$C_1$–$C_6$-alkyl, in particular mercaptomethyl, $C_1$–$C_4$-alkylthio-$C_1$–$C_6$-alkyl, in particular methylthioethyl, $C_1$–$C_6$-alkylsulphonyl-$C_1$–$C_6$-alkyl, in particular methylsulphinylethyl, $C_1$–$C_6$-alkyl-sulphonyl-$C_1$$C_4$-alkyl, in particular methylsulphonyl-ethyl, carboxy-$C_1$–$C_6$-alkyl, in particular carboxy-methyl, carboxyethyl, $C_1$–$C_4$-alkoxycarbonyl-$C_1$–$C_6$-alkyl, in particular methoxycarbonylmethyl, ethoxycarbonylethyl, $C_1$–$C_4$-arylalkoxycarbonyl-$C_1$–$C_6$-alkyl, in particular benzyloxycarbonylmethyl, carbamoyl-$C_1$–$C_6$-alkyl, in particular carbamoylmethyl, carbamoylethyl, amino-$C_1$–$C_6$-alkyl, in particular aminopropyl, aminobutyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, aryl, phenyl-$C_1$–$C_4$-alkyl, in particular phenylmethyl which can optionally be substituted by radicals from the series comprising halogen, in particular fluorine, chlorine, bromine or iodine, hydroxyl, $C_1$–$C_4$-alkoxy, in particular methoxy or ethoxy, $C_1$–$C_4$-alkyl, in particular methyl, nitro or a radical —$NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which is optionally substituted by $C_1$–$C_4$-alkyl, or represent hetarylmethyl, in particular benzo[b]thien-2-yl-methyl, benzo[b]thien-3-yl-methyl, naphth-1-yl-methyl, naphth-2-yl-methyl, pyrid-2-yl-methyl, pyrid-3-yl-methyl, fur-2-yl-methyl, fur-3-yl-methyl, indol-3-yl-methyl, N-methyl-indol-3-yl-methyl, imidazol-4-yl-methyl, N-methyl-imidazol-4-yl-methyl, B represents hydroxyl, tert-butoxy or the radical $NR^7R^8$, in which $R^7$ and $R^8$ independently of one another represent hydrogen, straight-chain or branched $C_{1-6}$-alkyl, in particular methyl, ethyl, isopropyl, tert-butyl, benzyl, cyclopropyl, cyclohexyl, phenyl, and their optical isomers and racemates. Compounds of the formula (I) which are particularly preferably used according to the invention are those in which A represents hydrogen, benzyl or a group $COR^9$, $R^9$ represents straight-chain or branched alkoxy or arylalkoxy having up to 6 carbon atoms in the alkyl moiety, in particular tert-butoxy or benzyloxy, $R^1$ and $R^4$ independently of one another represent hydrogen, $C_1$–$C_4$-alkyl, $C_3$–$C_6$-cycloalkyl or benzyl, $R^2$ and $R^5$ independently of one another represent hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, hydroxy-$C_1$–$C_6$-alkyl, in particular hydroxymethyl, 1-hydroxyethyl, $C_1$–$C_4$-alkanoyloxy-$C_1$–$C_6$-alkyl, in particular acetoxymethyl, 1-acetoxyethyl, $C_1$–$C_4$-alkoxy-$C_1$–$C_6$-alkyl, in particular methoxymethyl, 1-methoxyethyl, aryl-$C_1$–$C_4$-alkyloxy-$C_1$–$C_6$-alkyl, in particular benzyloxymethyl, 1-benzyloxyethyl, $C_1$–$C_4$-alkoxycarbonylamino-$C_1$–$C_6$-alkyl, in particular tert-butoxycarbonylaminopropyl, tert-butoxycarbonylaminobutyl, $C_2$–$C_8$-alkenyl, in particular vinyl, allyl, $C_3C_7$-cycloalkyl, in particular cyclopentyl, cyclohexyl, cycloheptyl, $C_3$–$C_7$-cycloalkyl-$C_1$–$C_4$-alkyl, in particular cyclopentylmethyl, cyclohexylmethyl, cycloheptylmethyl, phenyl, pyridyl, phenyl-$C_1$–$C_4$-alkyl, in particular phenylmethyl, it being possible for these to be optionally substituted by one or more identical or different radicals from amongst those listed above, $R^3$ and $R^6$ independently of one another represent hydrogen, straight-chain or branched $C_1$–$C_8$-alkyl, in particular methyl, ethyl, propyl, isopropyl, butyl, isobutyl, sec-butyl, tert-butyl, pentyl, isopentyl, sec pentyl, hexyl, isohexyl, sec-hexyl, heptyl, isoheptyl, sec-heptyl, tert-heptyl, octyl, isooctyl, sec-octyl, hydroxy-$C_1$–$C_6$-alkyl, in particular hydroxymethyl, aryl-$C_1$–$C_4$-alkyloxy-$C_1$–$C_6$-alkyl, in particular benzyloxymethyl, 1-benzyloxyethyl, carboxy-$C_1$–$C_6$-alkyl, in particular carboxymethyl, carboxyethyl, $C_1$–$C_4$-alkoxycarbonyl-$C_1$–$C_6$-alkyl, in particular methoxycarbonylmethyl; ethoxycarbonyl ethyl, $C_1$–$C_4$-arylalkoxycarbonyl-$C_1$–$C_6$-alkyl, in particular benzyloxycarbonylmethyl, $C_1$–$C_4$-alkylamino-$C_1$–$C_6$-alkyl, in particular methylaminopropyl, methylaminobutyl, $C_1$–$C_4$-dialkylamino-$C_1$–$C_6$-alkyl, in particular dimethylaminopropyl, dimethylaminobutyl, $C_2$–$C_8$-alkenyl, in particular vinyl, allyl, butenyl, $C_3$–$C_7$-cycloalkyl, in particular cyclopentyl, cyclohexyl, cycloheptyl, $C_3$-$C_7$-cycloalkyl-$C_1$–$C_4$-alkyl, in particular cyclopentylmethyl, cyclohexylmethyl, cycloheptylmethyl, hetaryl, phenyl, pyridylmethyl, phenyl-$C_1$–$C_4$-alkyl, in particular phenylmethyl, it being possible for these to be optionally substituted by one or more identical or different radicals from amongst those mentioned above, B represents hydroxyl or tert-butoxy, and their optical isomers and racemates.

Compounds of the formula (I) which are very particularly preferably used according to the invention are those in which A represents hydrogen or benzyl, $R^1$ and $R^4$ independently of one another represent hydrogen, methyl, ethyl, propyl and iso-propyl, $R^2$ and $R^5$ independently of one another represent hydrogen, straight-chain or branched $C_1$–$C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2$–$C_8$-alkenyl, in particular allyl, $C_3$–$C_7$-cycloalkyl-$C_1$–$C_4$-alkyl, in particular cyclohexylmethyl, phenyl-$C_1$–$C_4$-alkyl, in particular phenylmethyl, $R^3$ and $R^6$ independently of one another hydrogen, straight-chain or branched $C_1-C_8$-alkyl, in particular methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, $C_2-C_8$-alkenyl, in particular vinyl, allyl, $C_3-C_7$-cycloalkyl-$C_1-C_4$-alkyl, in particular cyclohexylmethyl, pyridylmethyl, phenyl-$C_1-C_4$-alkyl, in particular phenylmethyl, it being possible for these to be optionally substituted by one or more identical or different radicals from amongst those mentioned above, B represents hydroxyl or tert-butoxy,
and their optical isomers and racemates.

The following compounds of the general formula (I) in which the radicals A, $R^1$ to $R^6$ and B have the meanings given in the Table which follows may be mentioned individually:

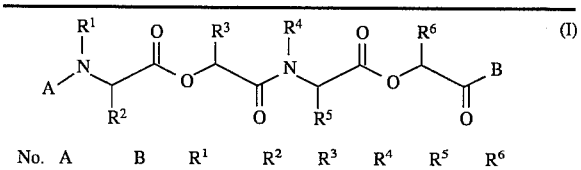

| No. | A | B | $R^1$ | $R^2$ | $R^3$ | $R^4$ | $R^5$ | $R^6$ |
|---|---|---|---|---|---|---|---|---|
| 1 | Bzl | O$^t$Bu | Me | $^i$Bu | Me | Me | $^i$Pr | Bzl |
| 2 | H | O$^t$Bu | Me | $^i$Bu | Me | Me | $^i$Pr | Bzl |
| 3 | Bzl | OH | Me | $^i$Bu | Me | Me | $^i$Pr | Bzl |
| 4 | Bzl | O$^t$Bu | Me | $^i$Pr | Me | Me | $^i$Bu | Bzl |
| 5 | Bzl | O$^t$Bu | Me | $^s$Bu | Me | Me | $^s$Bu | Bzl |
| 6 | H | O$^t$Bu | Me | $^i$Pr | Me | Me | $^i$Pr | Bzl |
| 7 | H | O$^t$Bu | Me | $^s$Bu | Me | Me | $^s$Bu | Bzl |
| 8 | H | O$^t$Bu | Me | $^i$Bu | Me | Me | $^i$Bu | Bzl |
| 9 | Bzl | O$^t$Bu | Pr | $^i$Bu | Me | Pr | $^i$Bu | Bzl |
| 10 | Bzl | O$^t$Bu | Et | $^i$Bu | Me | Et | $^i$Bu | Bzl |
| 11 | Bzl | O$^t$Bu | $^i$Pr | $^i$Bu | Me | $^i$Pr | $^i$Bu | Bzl |
| 12 | H | O$^t$Bu | Pr | $^i$Bu | Me | Pr | $^i$Bu | Bzl |
| 13 | H | O$^t$Bu | Et | $^i$Bu | Me | Et | $^i$Bu | Bzl |
| 14 | Bzl | OH | Pr | $^i$Bu | Me | Pr | $^i$Bu | Bzl |
| 15 | Bzl | OH | Et | $^i$Bu | Me | Et | $^i$Bu | Bzl |
| 16 | Bzl | OH | $^i$Pr | $^i$Bu | Me | $^i$Pr | $^i$Bu | Bzl |
| 17 | H | O$^t$Bu | $^i$Pr | $^i$Bu | Me | $^i$Pr | $^i$Bu | Bzl |
| 18 | Bzl | O$^t$Bu | Me | Bzl | Me | Me | Bzl | Bzl |
| 19 | H | O$^t$Bu | Me | Bzl | Me | Me | Bzl | Bzl |
| 20 | Bzl | OH | Me | Bzl | Me | Me | Bzl | Bzl |
| 21 | H | OH | Pr | $^i$Bu | Me | Pr | $^i$Bu | Bzl |
| 22 | Bzl | O$^t$Bu | Me | $^i$Bu | Me | Me | $^i$Bu | 2-Cl-Bzl |
| 23 | H | O$^t$Bu | Me | $^i$Bu | Me | Me | $^i$Bu | 2-Cl-Bzl |
| 24 | Bzl | OH | Me | $^i$Bu | Me | Me | $^i$Bu | 2-Cl-Bzl |
| 25 | Bzl | O$^t$Bu | Me | Me | Me | Me | Me | Bzl |
| 26 | H | O$^t$Bu | Me | Me | Me | Me | Me | Bzl |
| 27 | Bzl | OH | Me | Me | Me | Me | Me | Bzl |
| 28 | Bzl | O$^t$Bu | Me | Pr | Me | Me | Pr | Bzl |
| 29 | Bzl | O$^t$Bu | Me | $^s$Bu | $^i$Pr | Me | Bzl | $^i$Pr |
| 30 | Bzl | O$^t$Bu | Me | $^s$Bu | $^i$Pr | Me | Bzl | $^i$Pr |
| 31 | Bzl | O$^t$Bu | Me | $^i$Bu | Me | Me | $^i$Bu | Me |
| 32 | H | O$^t$Bu | Me | $^i$Bu | Me | Me | $^i$Bu | Me |
| 33 | Bzl | O$^t$Bu | Me | $^s$Bu | Me | Me | $^s$Bu | Me |
| 34 | H | O$^t$Bu | Me | $^s$Bu | Me | Me | $^s$Bu | Me |
| 35 | H | O$^t$Bu | Me | n-Bu | Me | Me | Bu | Me |
| 36 | Bzl | OH | Me | $^s$Bu | Me | Me | $^s$Bu | Me |
| 37 | Bzl | O$^t$Bu | Pr | Me | Me | Pr | Me | Me |
| 38 | Bzl | O$^t$Bu | $^i$Pr | Me | Me | $^i$Pr | Me | Me |
| 39 | Bzl | O$^t$Bu | Bzl | Bzl | Me | Bzl | Me | Me |
| 40 | Bzl | O$^t$Bu | $^s$Bu | Bzl | Me | $^s$Bu | Me | Me |
| 41 | Bzl | O$^t$Bu | Me | $^i$Bu | H | Me | $^i$Bu | H |
| 42 | H | O$^t$Bu | Me | $^i$Bu | Me | Me | $^i$Bu | H |
| 43 | Bzl | OH | Me | $^i$Bu | Me | Me | $^i$Bu | Me |
| 44 | Bzl | OH | Me | $^i$Bu | H | Me | $^i$Bu | H |
| 45 | H | O$^t$Bu | Me | $^i$Bu | H | Me | $^i$Bu | H |
| 46 | H | OH | Me | $^i$Bu | Me | Me | $^i$Bu | Me |
| 47 | H | OH | Me | $^s$Bu | Me | Me | $^s$Bu | Me |
| 48 | H | OH | Me | Pr | Me | Me | Pr | Me |

Bzl = benzyl
Bu = butyl

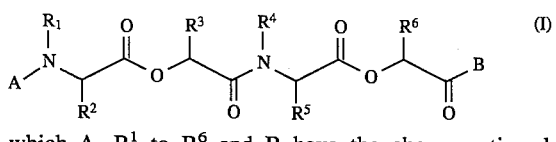

| No. | A | B | $R^1$ | $R^2$ | $R^3$ | $R^4$ | $R^5$ | $R^6$ |

Me = methyl
Pr = propyl
Et = ethyl

The compounds of the general formula (I) can exist in optically active, stereoisomeric forms or in the form of racemic mixtures. However, the optically active forms of the compounds of the general formula (I) are preferably used.

The preparation of the open-chain tetradepsipeptides of the general formula (I) to be used according to the invention is described in earlier, but not prior-published, patent applications (cf. German Patent Applications P 43 17 457.4; P 43 17 432.9, P 43 17 458.2).

Compounds of the formula (I)

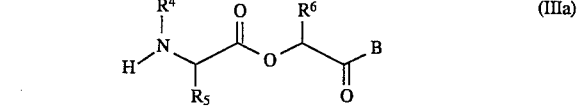

in which A, $R^1$ to $R^6$ and B have the abovementioned meaning are obtained, for example, when didepsipeptides of the general formula (IIa)

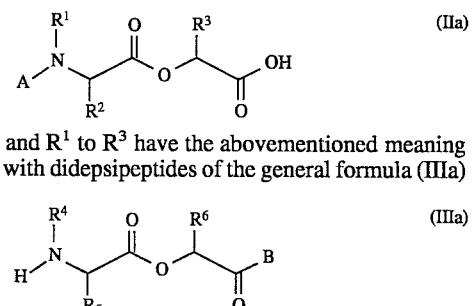

in which A and $R^1$ to $R^3$ have the abovementioned meaning are reacted with didepsipeptides of the general formula (IIIa)

in which B and $R^4$ to $R^6$ have the meaning given further above in the presence of suitable coupling reagents, in the presence of a basic reaction auxiliary and in the presence of a diluent to give the tetradepsipeptides of the general formula (I).

The didepsipeptides according to the invention which are used as starting compounds can be prepared by traditional processes, for example the process described by yon H.-G. Lerchen and H. Kunz (Tetrahedron Lett. 26 (43) (1958) pp. 5257–5260; 28 (17) (1987) pp. 1873–1876), in which the esterification process described by B. F. Gisin (Helv. Chim. Acta 56 (1973) p. 1476) is used.

Some of the N-methyl-amino acids and 2-halogenocarboxylic acid derivatives used as starting materials are known (cf. for example N-methyl-amino acids: R. Bowmann et al., J. Chem. Soc. (1950), p. 1346; J. R. McDermott et al., Can. J. Chem. 51 (1973) p. 1915; H. Wurziger et al., Kontakte [Catalysts](Merck, Darmstadt) 3 (1987) p. 8; 2-halogenocarboxylic acid derivatives: S. M. Birnbaum et al., J. Amer. Chem. Soc. 76 (1954), p. 6054, C. S. Rondestvedt, Jr. Et al., Org. Reactions 11 (1960) p. 189 (Review)) or can be obtained by the processes described in these publications.

Coupling reagents which are used for the coupling reaction of the didepsipeptides (IIa), (IIa) employed as starting compounds are all those which are suitable for producing an amide linkage (cf. for example: Houben-Weyl, Methoden der organischen Chemie [Methods in Organic Chemistry], Vol. 15/2; Bodanszky et al., Peptide Synthesis 2nd ed. (Wiley & Sons, New York 1976) or Gross, Meienhofer, The Peptides: Analysis synthesis, biology (AWcademic Press, New York 1979).

The open-chain tetradepsipeptides of the formula (I) can therefore be obtained in accordance with a reaction sequence which embraces the following steps:

a) Synthesis of the didepsipeptides of the formulae (II) and (III):

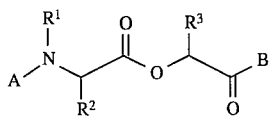

(II)

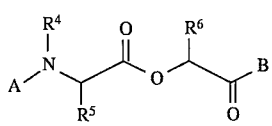

(III)

in which A denotes an N-terminal protective group such as, for example, the benzyl or benzyloxy-carbonyl group and B denotes a C-terminal protective group such as, for example, the tert-butoxy group.

In the case of formula (II), for example, this follows the equation below:

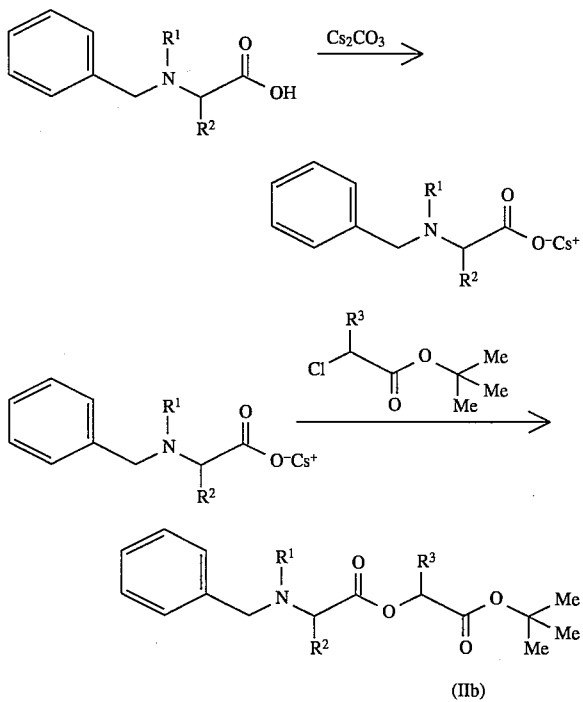

(IIb)

If appropriate, the enantiomerically pure compounds of the formulae (II) and (III) can also be prepared by means of diastereomer separation by customary methods such as, for example, crystallization, by column chromatography or by countercurrent distribution. The best possible process will have to be decided in each individual case; sometimes it is also expedient to use combinations of the individual processes.

At the end of this step, either the N-terminal protective group can be removed from the derivatives of the formula (III) in a manner known per se, for example by catalytic hydrogenation, to prepare the derivatives of the formula (IIIa'), or else the C-terminal protective group can be eliminated from the derivatives of the formula (II) in a manner known per se, preferably by acidolysis, to synthesize the derivatives (IIa'):

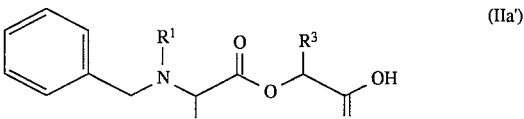

(IIa')

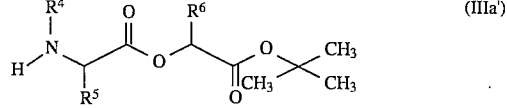

(IIIa')

b) Synthesis of the tetradepsipeptide of the formula (I)

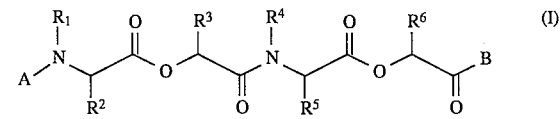

(I)

in the case of formula (I), this corresponds to the equation which follows:

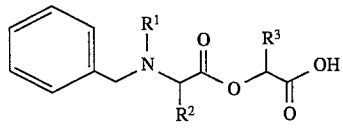

(IIa')

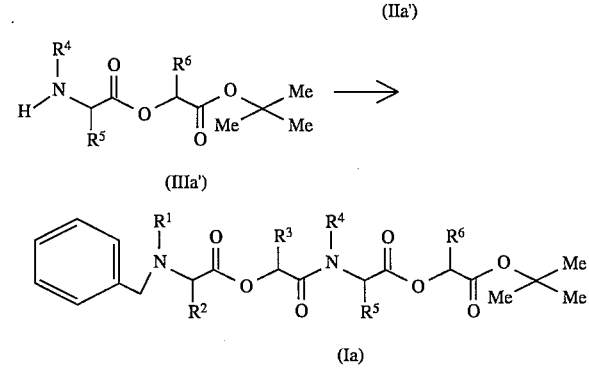

(Ia)

The N-terminal protective group may subsequently be removed from the derivatives of the formula (Ia), for example by catalytic hydrogenation as described above, to prepare the derivatives of the formula (Ic),

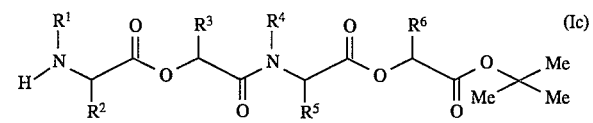

(Ic)

or else the C-terminal protective group can be eliminated in a manner known per se, preferably by acidolysis, to synthesize the derivatives (Ib)

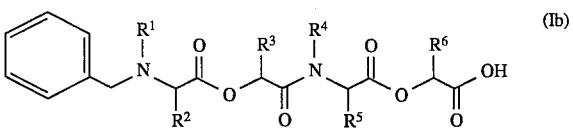

(Ib)

The products obtained can be purified in the customary manner by recrystallization or column chromatography (cf. also the preparation examples).

While having favourable toxicity to warm-blooded species, the active compounds are suitable for combating pathogenic endoparasites which occur in humans and in animal keeping and livestock breeding, in productive livestock, breeding animals, zoo animals, laboratory animals, experimental animals and pets. In this context, they are active against all or individual stages of development of the pests and against resistant and normally-sensitive species. By combating the pathogenic endoparasites, it is intended to reduce disease, deaths and decreasing performance (for example in the production of meat, milk, wool, hides, eggs, honey etc.), so that more economical and simpler animal keeping is possible by using the active compounds. The pathogenic endoparasites include Cestodes, Treatodes, Nematodes and Acantocephala, in particular:

From the order of the Pseudophyllidea, for example: Diphyllobothrium spp., Spirometra spp., Schistocephalus spp., Ligula spp., Bothridium spp., Diphlogonoporus spp..

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the subclass of the Monogenea, for example: Gyrodactylus spp., Dactylogyrus spp., Polystoma spp..

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoton spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonismus spp..

From the order of the Enoplida, for example: Trichuris spp., Capillaria spp., Trichomosoides spp., Trichinella spp..

From the order of the Rhabditia, for example: Micronema spp., Strongyloides spp..

From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosomaspp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example: Oxyuris spp., Enterobius spp., Passalurus spp., Syphacia spp., Aspiculuris spp., Heterakis spp..

From the order of the Ascaridia, for example: Ascaris spp., Toxascaris spp., Toxocara spp., Parascaris spp., Anisakis spp., Ascaridia spp..

From the order of the Spirurida, for example: Gnathostoma spp., Physaloptera spp., Thelazia spp., Gongylonema spp., Habronema spp., Parabronema spp., Draschia spp., Dracunculus spp..

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example: Filicollis spp., Moniliformis spp., Macracanthorhynchus spp., Prosthenorchis spp..

The productive livestock and breeding animals include meals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carps, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically.

The active compounds are administered, directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, tablets, capsules, pastes, drinks, granules, or solutions, suspensions and emulsions which can be administered orally, or boli, medicated feed or drinking water. Dermal administration is effected, for example, in the form of dipping, spraying or pouring-on and spotting-on. Parenteral administration is effected, for example, in the form of injection (intramuscularly, subcutaneously, intravenously, intraperitoneally) or by implants.

Suitable preparations are:

Solutions such as injectable solutions, oral solutions, concentrates for oral administration after dilution, solutions for use on the skin or in body cavities, pour-on and spot-on formulations, gels;

Emulsions and suspensions for oral or dermal administration and for injection; semi-solid preparations;

formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, active-compound-containing shaped articles. Injectable solutions are administered intravenously, intramuscularly and subcutaneously.

Solutions for injection are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the solutions for injection, it being possible to dispense with working under sterile conditions.

Solutions for use on the skin are applied dropwise, brushed on, rubbed in, splashed on or sprayed on. These solutions are prepared as described above in the case of the solutions for injection.

It may be advantageous to add thickeners during the preparation. Thickeners are: inorganic thickeners such as bentonite, colloidal silica, aluminium monostearate, organic thickeners such as cellulose derivatives, polyvinyl alcohols and their copolymers, acrylates and methacrylates.

Gels are applied to, or brushed on, the skin, or introduced into body cavities. Gels are prepared by treating solutions which have been prepared as described in the case of the solutions for injection with such an amount of thickener that a clear substance of ointment-like consistency is formed. Thickeners employed are the thickeners indicated further above.

Pour-on and spot-on formulations are poured onto, or splashed onto, limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other adjuvants such as colourants, resorption accelerators, antioxidants, light stabilizers, and tackifiers are added.

The following may be mentioned as solvents: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ethers, diethylene glycol mono-butyl ethers, ketones such as acetone, methyl ethyl ketone, aromatic and/or aliphatic hydrocarbons, vegetable or synthetic oils, DMF, dimethylacetamide, N-methylpyrrolidone, 2,2-dimethyl-4-oxy-methylene-1,3-dioxolane.

Colourants are all colourants which are licensed for use on animals and which can be dissolved or suspended.

Examples of resorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenising this phase with the solvent of the other phase, with the aid of suitable emulsifiers and, if appropriate, other adjuvants such as colourants, resorption accelerators, preservatives, antioxidants, light stabilizers, viscosity-increasing substances.

The following may be mentioned as hydrophobic phase (oils): paraffin oils, silicone oils, natural vegetable oils such as sesame seed oil, almond oil, castor oil, synthetic triglycerides such as caprylic/capric acid bigylceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}-C_{18}$, isopropyl myristate, isopropyl palmitate, caprylic/capric esters of saturated fatty alcohols of chain length $C_{12}-C_{18}$, isopropyl stearate, oleyl oleate, decyl oleate, ethyl oleate, ethyl lactate, waxy fatty acid esters such as artificial uropygial gland fat from ducks, dibutyl phthalate, diisopropyl adipate, ester mixtures related to the latter, and the like.

Fatty alcohols such as isotridecyl alcohol, 2-octyl dodecanol, cetylstearyl alcohol, oleyl alcohol.

Fatty acids such as, for example, oleic acid and its mixtures.

The following may be mentioned as hydrophilic phase: water, alcohol such as, for example, propylene glycol, glycerol, sorbitol and their mixtures.

The following may be mentioned as emulsifiers: nonionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as Na-lauryl sulphate, fatty alcohol ether sulphates, the monoethynol amine salt of mono/dialkylpolyglycol ether orthophosphoric esters;

The following may be mentioned as other adjuvants: viscosity-increasing substances and substances which stabilise the emulsion, such as carboxymethylcellulose, methylcellulose and other cellulose and starch derivatives, polyacrylates, alginates, gelatine, gum arabic, polyvinyl pyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of injection. They are prepared by suspending the active substance in an excipient liquid, if appropriate with the addition of further adjuvants such as wetting agents, colourants, resorption accelerators, preservatives, antioxidants and light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, animal meals, cereal meals and coarse cereal meals and starches.

Adjuvants are preservatives, antioxidants and colourants which have already been indicated further above.

Other suitable adjuvants are the lubricants and gliding agents such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazothiazole, benzimidazole carbamates, praziquantel, pyrantel, febantel.

Ready-to-use preparations contain the active compound in concentrations of from 10 ppm to 20 percent by weight, preferably of from 0.1 to 10 percent by weight.

Preparations which are diluted prior to administration contain the active compound in concentrations of from 0.5 to 90 percent by weight, preferably of from 5 to 50 percent by weight.

In general, it has proved advantageous to administer amounts of approximately 1 to approximately 100 mg of active compound per kg of body weight per day, to achieve effective results.

Example A

In vivo nematode test

Haemonchus contortus/sheep

Sheep which had been infected experimentally with Haemonchus contortus were treated after the prepatency period of the parasites had elapsed. The active compounds were administered orally and/or intravenously in the form of the pure active compound.

The degree of effectiveness is determined by quantitatively determining the nematode eggs excreted with the faeces before and after the treatment.

If egg excretion stops completely after the treatment, this means that the nematodes have been aborted or damaged in such a manner that they no longer produce eggs (dosis effectiva).

Active compounds which have been tested and effective dosage rates (dosis effectiva) can be seen from the Table which follows:

| Active compound Example No. | Dosis effectiva in mg/kg |
| --- | --- |
| 1 | 10 |
| 2 | 10 |
| 3 | 10 |

PREPARATION EXAMPLES

Example 1 tert.-Butyl-N-ethyl-L-leucyl-D-lactyl-N-ethyl-L-leucyl-D-3-phenyllactate

Palladium hydroxide (0.73 g, 20%/charcoal) was added to a solution of Benzyl-L-EtLeu-D-Lac-L-EtLeu-PheLac-O$^t$Bu (7.83 g, 11.7 mmol) in dioxane (50 ml), and the mixture was hydrogenated at room temperature under atmospheric pressure until hydrogen was no longer taken up. After filtration through Celite, 7.48 g (984) of pure H-L-EtLeu-D-Lac-L-EtLeu-D-pheLac-O$^t$Bu were obtained. FAB-MS m/z (%): 577 (62, (M+H))$^+$·158 (100).

Example 2

N-Benzyl-N-propyl-L-leucyl-D-lactyl-N-propyl-L-leucyl-D-phenyllactic acid

HCl(g) was passed for 2 hours at 0° C. into a solution of Bzl-L-PrLeu-D-Lac-L-PrLeu-D-PheLac-O$^t$Bu (9.12 g, 13.2 mmol) in dichloromethane (235 ml), and stirring was continued overnight at room temperature. The mixture was subsequently concentrated and codistilled twice with dichloromethane. The residue was taken up in MeOH/H$_2$O=4:1, 5.5 g of basic ion exchanger were added, and the mixture was stirred for 2 hours. After the ion exchanger had been filtered off and the filtrate had been concentrated, 8.1 g (964) of Bzl-L-PrLeu-D-Lac-L-PrLeu-D-PheLac-OH remained.

FAB-MS m/z (%): 639 (32, M+H)$^+$.), 262 (92%), 218 (108).

Example 3 tert.-Butyl-N-methyl-L-phenylalanyl-D-lactyl-N-methyl-D-phenylalanyl-D-lactate

Pd(OH)$_2$/C (20%, 320 mg) is added to a solution of Bzl-L-MePhe-D-Lac-L-MePhe-D-PheLac-O$^t$Bu (3.2 g, 4.53 mmol) in ethanol (20 ml), and the mixture is hydrogenated at room temperature and under atmospheric pressure until hydrogen is no longer taken up. After filtration through Celite, 2.29 g (82%) of H-L-MePhe-D-Lac-L-MePhe-D-PheLac-O$^t$Bu are obtained.

Example 4 tert. -Butyl-N-benzyl-N-methyl-L-leucyl-D-lactyl-N-methyl-L-leucyl,D-3-phenyllactate Diisopropylethylamine (9.98 ml, 57.3 mmol) and bis-(2-oxo-3-oxazolidinyl)-phosphinic chloride (7.59 g, 29.8 mmol) were added to a solution, cooled to 0° C., of H-L-MeLeu-D-PheLac-O$^t$Bu (8.0 g, 22.9 mmol) and Bzl-L-MeLeu-D-Lac-O$^1$Bu (8.44 g, 27.5 mmol) in dichloromethane (80 ml), and the mixture was stirred for i hour at 0° C and for 1 hour at room temperature. After the precipitate had been filtered off, the solution was diluted with dichloromethane, washed three times using a small amount of water, dried over sodium sulphate and concentrated. Flash chromatography on silica gel using cyclohexane/ethyl acetate=15:1 as the eluent gave 11.6 g (80%) of Bzl-L-MeLeu-D-Lac-L-MeLeu-D-PheLac-O$^t$Bu. FAB-MS m/z (%): 639 (37, (M+H)$^+$.), 190 (100).

The compounds of the general formula (I) listed in Table 2 below can be prepared analogously in the form of the LDLD stereoisomers.

$$\underset{R^2}{\overset{R^1}{A-N}}-\overset{O}{\underset{}{\overset{}{C}}}-O-\underset{}{\overset{R^3}{C}}-\underset{O}{\overset{}{\overset{}{C}}}-\underset{R^5}{\overset{R^4}{N}}-\underset{}{\overset{}{\overset{}{C}}}-O-\underset{}{\overset{R^6}{C}}-\underset{O}{\overset{}{\overset{}{C}}}-B,\quad (I)$$

| Ex. No. | A | B | R¹ | R² | R³ | R⁴ | R⁵ | R⁶ | Mass spectroscopy data |
|---|---|---|---|---|---|---|---|---|---|
| 5 | H | O$^t$Bu | Me | $^i$Bu | Me | Me | $^i$Pr | Bzl | 548 (1, M⁺) |
| 6 | Bzl | OH | Me | $^i$Bu | Me | Me | $^i$Pr | Bzl | 582 (0.5, M⁺) |
| 7 | Bzl | O$^t$Bu | Me | $^i$Pr | Me | Me | $^i$Bu | Bzl | 611 (64, (M + H)⁺) |
| 8 | Bzl | O$^t$Bu | Me | $^s$Bu | Me | Me | $^s$Bu | Bzl | 639 (92, (M + H)⁺) |
| 9 | H | O$^t$Bu | Me | $^i$Pr | Me | Me | $^i$Pr | Bzl | 521 (100, (M + H)⁺) |
| 10 | H | O$^t$Bu | Me | $^s$Bu | Me | Me | $^s$Bu | Bzl | 549 (76, (M + H)⁺) |
| 11 | H | O$^t$Bu | Me | $^i$Bu | Me | Me | $^i$Bu | Bzl | 548 (100, M⁺) |
| 12 | Bzl | O$^t$Bu | Pr | $^i$Bu | Me | Pr | $^i$Bu | Bzl | 695 (86, (M + H)⁺) |
| 13 | Bzl | O$^t$Bu | Et | $^i$Bu | Me | Et | $^i$Bu | Bzl | 667 (70, (M + H)⁺) |
| 14 | Bzl | O$^t$Bu | $^i$Pr | $^i$Bu | Me | $^i$Pr | $^i$Bu | Bzl | 695 (28, (M + H)⁺) |
| 15 | H | O$^t$Bu | Pr | $^i$Bu | Me | Pr | $^i$Bu | Bzl | 605 (100, (M + H)⁺) |
| 16 | Bzl | OH | Et | $^i$Bu | Me | Et | $^i$Bu | Bzl | 611 (36, (M + H)⁺) |
| 17 | Bzl | OH | $^i$Pr | $^i$Bu | Me | $^i$Pr | $^i$Bu | Bzl | 639 (82, M⁺) |
| 18 | H | O$^t$Bu | $^i$Pr | $^i$Bu | Me | $^i$Pr | $^i$Bu | Bzl | 605 (100, M⁺) |
| 19 | Bzl | O$^t$Bu | Me | Bzl | Me | Me | Bzl | Bzl | 707 (15, M⁺) |
| 20 | Bzl | OH | Me | Bzl | Me | Me | Bzl | Bzl | 651 (64, (M + H)⁺) |
| 21 | H | OH | Pr | $^i$Bu | Me | Pr | $^i$Bu | Bzl | |
| 22 | Bzl | O$^t$Bu | Me | $^i$Bu | Me | Me | $^i$Bu | 2-Cl-Bzl | 673 (100, (M + H)⁺) |
| 23 | H | O$^t$Bu | Me | $^i$Bu | Me | Me | $^i$Bu | 2-Cl-Bzl | 583 (24, (M + H)⁺) |
| 24 | Bzl | OH | Me | $^i$Bu | Me | Me | $^i$Bu | 2-Cl-Bzl | 617 (36, (M + H)⁺) |
| 25 | Bzl | O$^t$Bu | Me | Me | Me | Me | Me | Bzl | 555 (52, (M + H)⁺) |
| 26 | H | O$^t$Bu | Me | Me | Me | Me | Me | Bzl | |
| 27 | Bzl | OH | Me | Me | Me | Me | Me | Bzl | 499 (10, (M + H)⁺) |
| 28 | Bzl | O$^t$Bu | Me | Pr | Me | Me | Pr | Bzl | 611 (100, (M + H)⁺) |
| 29 | Bzl | O$^t$Bu | Me | $^s$Bu | $^i$Pr | Me | Bzl | $^i$Pr | |
| 30 | Bzl | O$^t$Bu | Me | $^s$Bu | $^i$Pr | Me | Bzl | $^i$Pr | 652 (8, M⁺) |
| 31 | Bzl | O$^t$Bu | Me | $^i$Bu | Me | Me | $^i$Bu | Me | 562 (3, M⁺) |
| 32 | H | O$^t$Bu | Me | $^i$Bu | Me | Me | $^i$Bu | Me | 472 (4, M⁺) |
| 33 | Bzl | O$^t$Bu | Me | $^s$Bu | Me | Me | $^s$Bu | Me | 563 (1, (M + H)⁺) |
| 34 | H | O$^t$Bu | Me | $^s$Bu | Me | Me | $^s$Bu | Me | 472 (1, M⁺) |
| 35 | H | O$^t$Bu | Me | n-Bu | Me | Me | n-Bu | Me | 472 (1, M⁺) |
| 36 | Bzl | OH | Me | $^s$Bu | Me | Me | $^s$Bu | Me | 506 (3, M⁺) |
| 37 | Bzl | O$^t$Bu | Me | Pr | Me | Me | Pr | Me | 534 (2, (M⁺)) |
| 38 | Bzl | O$^t$Bu | Me | $^i$Pr | Me | Me | $^i$Pr | Me | 534 (6, M⁺) |
| 39 | Bzl | O$^t$Bu | Me | Bzl | Bzl | Me | Bzl | Me | 707 (5, (M + H)⁺) |
| 40 | Bzl | O$^t$Bu | Me | $^s$Bu | Bzl | Me | $^s$Bu | Me | 638 (5, M⁺) |
| 41 | Bzl | O$^t$Bu | Me | $^i$Bu | H | Me | $^i$Bu | H | |
| 42 | H | O$^t$Bu | Me | $^i$Bu | Me | Me | $^i$Bu | H | |
| 43 | Bzl | OH | Me | $^i$Bu | Me | Me | $^i$Bu | Me | |
| 44 | Bzl | OH | Me | $^i$Bu | H | Me | $^i$Bu | H | |

-continued

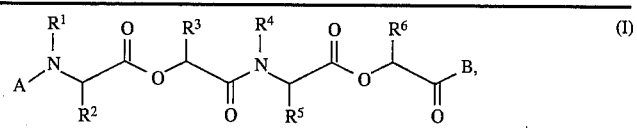

| Ex. No. | A | B | R¹ | R² | R³ | R⁴ | R⁵ | R⁶ | Mass spectroscopy data |
|---|---|---|---|---|---|---|---|---|---|
| 45 | H | OtBu | Me | iBu | H | Me | iBu | H | |
| 46 | H | OH | Me | iBu | Me | Me | iBu | Me | |
| 47 | H | OH | Me | sBu | Me | Me | sBu | Me | |
| 48 | H | OH | Me | Pr | Me | Me | Pr | Me | |

Preparation of the starting substances of the formulae II and III

Example II-1 tert.-Butyl-N-benzyl-N-methyl-L-leucyl-D-lactate

The caesium salt (77.7 g, 0.212 mol) in Bzl-L-MeLeu-OH was introduced into dimethyl sulphoxide (530 ml), and tert.-Butyl-2-chloro-propionate (34.76 g, 0.212 mol) was added at room temperature. The mixture was stirred for 20 hours at room temperature, poured into saturated sodium chloride solution and extracted four times using ethyl acetate. The combined organic extracts were washed once using a small amount of water, dried over sodium sulphate and concentrated. Column chromatography of the residue on silica gel using cyclohexane/ethyl acetate=60:1 as the eluent gave 63.5 g (82%) of Bzl-L-MeLeu-D-Lac-OtBu. Ei-MS m/z (%): 363 (M+, 1), 190 (100).

Example III-1 tert.-Butyl-N-benzyl-N-methyl-L-leucyl-D-3-phenyllactate

Bzl-L-MeLeu-OH (50.0 g, 0.212 mol), was dissolved in ethanol (1000 ml) water (100 ml), 20% strength caesium carbonate solution (41.5 g, 0.127 mol) in water was added, and the mixture was stirred for 5 hours at room temperature. The mixture was subsequently concentrated, codistilled twice using in each case 250 ml of DMF, and dried overnight under a high vacuum at 80° C. The caesium salt (77.7 g, 0.212 mol) was introduced into dimethyl sulphoxide (530 ml), tert-butyl 2-chloro-3-phenyl-propionate (51.0 g, 0.212 mol) was added at room temperature, and the mixture was stirred for 20 hours at room temperature.

The solution was poured into saturated sodium chloride solution, the mixture was extracted four times using ethyl acetate, and the extract was dried over sodium sulphate and concentrated. Column chromatography of the residue on silica gel using cyclohexane/ethyl acetate=100:1 as the eluent gave 26.6 g (294) of pure Bzl-L-MeLeu-D-PheLac-OBu and 48.9 g (52%) of a mixed fraction contaminated with tert-butyl cinnamate. Ei-MS m/z (%): 363 (1), 190 (100).

The compounds listed in the table which follows can be prepared analogously in the form of the L-D stereoisomers.

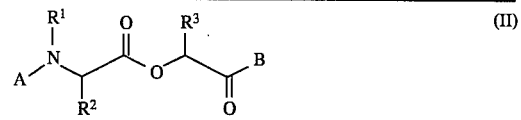

| Ex. No. | A | R¹ | R² | R³ | B | Mass spectroscopy data |
|---|---|---|---|---|---|---|
| II-2 | Bzl | Me | —(CH₂)₂—S-Me | Bzl | OtBu | 458 (100, (M + H)+) |
| II-3 | Bzl | Me | —(CH₂)₂—S-Me | Me | OtBu | 382 (100, (M + H)+) |
| II-4 | Bzl | Me | Pr | Me | OH | 294 (100, (M + H)+) |
| II-5 | H | Me | Pr | Bzl | OtBu | 336 (100, (M + H)+) |
| II-6 | Bzl | Me | Pr | Bzl | OtBu | 425 (2, M+) |
| II-7 | Bzl | Me | Pr | Me | OtBu | 349 (5, M+) |
| II-8 | H | Me | Me | Bzl | OtBu | 308 (100, (M + H)+) |
| II-9 | Bzl | Me | Me | Bzl | OtBu | 398 (100, (M + H)+) |
| II-10 | Bzl | Me | Me | Me | OtBu | 322 (100, (M + H)+) |
| II-11 | Bzl | Me | Me | Me | OH | 265 (2, M+) |

-continued

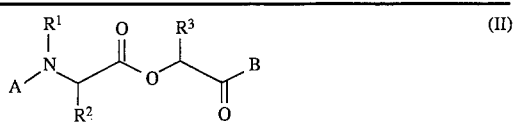

| Ex. No. | A | R¹ | R² | R³ | B | Mass spectroscopy data |
|---|---|---|---|---|---|---|
| II-12 | H | Me | iBu | p-Cl-Bzl | OtBu | 386 (100, (M + H)+) |
| II-13 | H | Me | iBu | p-Cl-Bzl | OtBu | 384 (36, (M + H)+) |
| II-14 | Bzl | Et | iBu | Me | OH | 322 (46, (M + H)+) |
| II-15 | Bzl | iPr | iBu | Me | OH | 336 (100, (M + H)+) |
| II-16 | Bzl | Pr | iBu | Me | OH | 336 (100, (M + H)+) |
| II-17 | H | Et | iBu | Bzl | OtBu | 363 (0.5, M+) |
| II-18 | H | iPr | iBu | Bzl | OtBu | |
| II-19 | H | Pr | iBu | Bzl | OtBu | 377 (0.4, M+) |
| II-20 | Bzl | Et | iBu | Bzl | OtBu | 454 (100, (M + H)+) |
| II-21 | Bzl | iPr | iBu | Bzl | OtBu | 467 (1 M+) |
| II-22 | Bzl | Pr | iBu | Bzl | OtBu | 468 (100, (M + H)+) |
| II-23 | Bzl | Et | iBu | Me | OtBu | 378 (100, (M + H)+) |
| II-24 | Bzl | iPr | iBu | Me | OtBu | 392 (100, (M + H)+) |
| II-25 | Bzl | Pr | iBu | Me | OtBu | 317 (46), 260 (42), 139(100) |
| II-26 | H | Me | Bzl | Bzl | OtBu | 383 (6, M+) |
| II-27 | Bzl | Me | Bzl | Bzl | OtBu | 400(2), 382(50), 326(36), 224(75) |
| II-28 | H | Me | sBu | Bzl | OtBu | 276(6), 236(15), 100(100) |
| II-29 | Bzl | Me | sBu | Me | OH | 307 (1, M+) |
| II-30 | Bzl | Me | iPr | Me | OH | 293 (2, M+) |
| II-31 | Bzl | Me | Bzl | Me | OH | 341 (1, M+) |
| II-32 | H | Me | iPr | Bzl | OtBu | |
| II-33 | Bzl | Me | sBu | Me | OtBu | 363 (1, M+) |
| II-34 | Bzl | Me | sBu | Bzl | OtBu | 439 (2, M+) |
| II-35 | Bzl | Me | iPr | Me | OtBu | 349 (3, M+) |
| II-36 | Bzl | Me | iPr | Bzl | OtBu | 425 (1, M+) |
| II-37 | Bzl | Me | Bzl | Me | OtBu | 397 (0.5, M+) |

We claim:

1. A method for combatting endoparasites in a human or animal host which comprises administering to said host an endoparasitically effective amount of an open-chain tetradepsipeptide of the formula

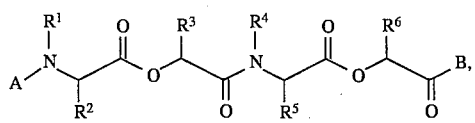

in which

A represents hydrogen, alkyl, aralkyl or an acyl radical of the formula —CO—R⁹, in which R⁹ represents straight-chain or branched alkyl, alkoxy, aralkyl or aralkoxy having up to 6 carbon atoms in the alkyl moiety, R¹ and R⁴ independently of one another represent hydrogen, $C_1$–$C_8$-alkyl, $C_3$–$C_6$-cycloalkyl or aralkyl, R² and R⁵ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which itself is optionally substituted by one or two benzyloxycarbonyl radicals or by one, two, three or four alkyl radicals, or represent alkoxycarbonylaminoalkyl, 9-fluorenylmethoxycarbonyl-(FMOC)aminoalkyl, alkenyl, cycloalkyl, cycloalkylalkyl and optionally substituted aryl, optionally substituted arylalkyl or optionally substituted hetarylmethyl, wherein the substituents are halogen, hydroxyl, alkyl, alkoxy, nitro or a radical —$NR^{10}R^{11}$, in which $R^{10}$ and $R^{11}$ independently of one another represent hydrogen or alkyl, or $R^{10}$ and $R^{11}$ together with the adjacent N atom represent a carbocyclic 5-, 6-, 7- or 8-membered ring which is optionally interrupted by O, S and N and which is optionally substituted by $C_1$–$C_4$-alkyl, $R^3$ and $R^6$ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl and optionally substituted aryl, optionally substituted arylalkyl or optionally substituted hetarylmethyl, wherein the substituents are halogen, hydroxyl, alkyl, alkoxy, nitro or a radical —$NR^{10}$—$R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which is optionally interrupted by O, S and N and which is optionally substituted by $C_1$–$C_4$-alkyl, B represents hydroxyl, alkoxy having up to 4 carbon atoms or the radical $NR^7R^8$, in which $R^7$ and $R^8$ represent hydrogen, alkyl, aralkyl or aryl, or its optical isomer or racemate.

2. The method according to claim 1, wherein

A represents hydrogen or $C_{1-4}$-alkyl or benzyl, or represents a group of the formula —CO—$R^9$, in which $R^9$ represents straight-chain or branched $C_{1-4}$-alkyl, $C_{2-4}$-alkenyl, $C_{1-4}$-alkoxy or phenyl-alkoxy having up to 6 carbon atoms in the alkyl moiety, $R^1$ and $R^4$ independently of one another represent hydrogen, $C_{1-6}$-alkyl, $C_{3-6}$-cycloalkyl, or phenyl-$C_{1-4}$-alkyl, $R^2$ and $R^5$ independently of one another represent hydrogen, methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxymethyl, 1-hydroxyethyl, acetoxymethyl, 1-acetoxyethyl, 1-methoxyethyl, benzyloxyethyl, 1-benzyl-oxy-ethyl, mercaptomethyl, methylthioethyl, methylsulphinylethyl, methylsulphonylethyl, carboxymethyl, carboxyethyl, methoxycarbonylmethyl, ethoxycarbonylethyl, benzyloxycarbonylmethyl, carbamoylmethyl, carbamoylethyl, aminopropyl, aminobutyl, methylaminopropyl, methylaminobutyl, dimethylaminopropyl, dimethylaminobutyl, guanidopropyl, tertbutoxycarbonylaminopropyl, tert-butoxycarbonylaminobutyl, 9-fluorenylmethoxycarbonyl(Fmoc)aminopropyl, 9-fluorenylmethoxycarbonyl(Fmoc)aminobutyl, vinyl, allyl, butenyl, cyclopentyl, cyclohexyl, cycloheptyl, cyclopentylmethyl, cyclohexylmethyl, cycloheptylmethyl, aryl, phenyl-$C_2$–$C_4$-alkyl which is optionally substituted by radicals selected from the group consisting of fluorine, chlorine, bromine, iodine, hydroxyl, methoxy, ethoxy, methyl, nitro and a radical —$NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which is optionally substituted by $C_1$–$C_4$-alkyl, or $R^2$ and $R^5$ or represent benzo thien-2-yl-methyl, benzothien-3-yl-methyl, naphth-1-yl-methyl, naphth-2-yl-methyl, pyrid-2-yl-methyl, pyrid-3-yl-methyl, fur-2-yl-methyl, fur-3-yl-methyl, indol-3-yl-methyl, N-methyl-indol- 3-yl-methyl, imidazol-4-yl-methyl, or N-methyl-imidazol-4-yl-methyl, $R^3$ and $R^6$ independently of one another represent hydrogen, methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxymethyl, 1-hydroxyethyl, $C_1$–$C_4$-alkanoyloxy-$C_1$–$C_6$-alkyl, acetoxymethyl, 1-acetoxyethyl, methoxymethyl, 1-methoxyethyl, benzyloxymethyl, 1-benzyloxyethyl, mercaptomethyl, methylthioethyl, methylsulphinylethyl, methylsulphonylethyl, carboxymethyl, carboxyethyl, methoxycarbonylmethyl, ethoxycarbonylethyl, benzyloxycarbonylmethyl, carbamoylmethyl, carbamoylethyl, aminopropyl, aminobutyl, methylaminopropyl, methylaminobutyl, dimethylaminopropyl, dimethylaminobutyl, vinyl, allyl, butenyl, cyclopentyl, cyclohexyl, cycloheptyl, cyclopentylmethyl, cyclohexylmethyl, cycloheptylmethyl, aryl, phenyl-$C_1$–$C_4$-alkyl, which is optionally substituted by radicals selected from the group consisting of fluorine, chlorine, bromine, iodine, methoxy, ethoxy, methyl, nitro and a radical —$NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which is optionally substituted by $C_1$–$C_4$-alkyl, or $R^3$ and $R^6$ represent benzothien-2-yl-methyl, benzothien-3-yl-methyl, naphth-1-yl-methyl, naphth-2-yl-methyl, pyrid-2-yl-methyl, pyrid-3-yl-methyl, fur-2-yl-methyl, fur-3-yl-methyl, indol-3-yl-methyl, N-methyl-indol- 3-yl-methyl, imidazol-4-yl-methyl, or N-methyl-imidazol-4-yl-methyl, B represents hydroxyl, tert-butoxy or the radical $NR^7R^8$, in which $R^7$ and $R^8$ independently of one another represent hydrogen, methyl, ethyl, isopropyl, tert-butyl, benzyl, cyclopropyl, cyclohexyl, or phenyl, or its optical isomer or racemate.

3. The method according to claim 1, wherein

A represents hydrogen benzyl or a group $COR^9$, $R^9$ represents alkyl, tert-butoxy, benzyloxy, ethoxy, allyloxy, fluorenyl-9-methoxy or methoxy, $R^1$ and $R^4$ independently of one another represent hydrogen, $C_1$–$C_4$-alkyl, $C_3$–$C_6$-cycloalkyl or benzyl, $R^2$ and $R^5$ independently of one another represent hydrogen, methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, hydroxymethyl, 1-hydroxyethyl, acetoxymethyl, 1-acetoxyethyl, methoxymethyl, 1-methoxyethyl, benzyloxymethyl, 1-benzyloxyethyl, tert-butoxycarbonylaminopropyl, tert-butoxycarbonylaminobutyl, vinyl, allyl, cyclopentyl, cyclohexyl, cycloheptyl, cyclopentylmethyl, cyclohexylmethyl, cycloheptylmethyl, optionally substituted phenyl, optionally substituted pyridyl, or optionally substituted phenylmethyl, wherein said substituents on phenyl or phenylmethyl are fluorine, chlorine, bromine or iodine and said substituents on pyridyl are $C_1$–$C_4$-alkyl, R³ and R⁶ independently of one another represent hydrogen, methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxymethyl, benzyloxymethyl, 1-benzyloxyethyl, carboxymethyl, carboxyethyl, methoxycarbonylmethyl, ethoxycarbonylethyl, benzyloxycarbonylmethyl, methylaminopropyl, methylaminobutyl, dimethylaminopropyl, dimethylaminobutyl, vinyl, allyl, butenyl, cyclopentyl, cyclohexyl, cycloheptyl, cyclopentylmethyl, cyclohexylmethyl, cycloheptylmethyl, optionally substituted hetaryl, optionally substituted phenyl, optionally substituted pyridylmethyl, or optionally substituted phenylmethyl, wherein said substituents on phenyl are fluorine, chlorine, bromine, or iodine and said substituents on hetaryl are $C_1$–$C_4$-alkyl, B represents hydroxyl or tert-butoxy, or its optical isomer or racemate.

4. The method according to claim 1, wherein

A represents hydrogen or benzyl,

R¹ and R⁴ independently of one another represent hydrogen, methyl, ethyl, propyl or iso-propyl, R² and R⁵ independently of one another represent hydrogen, methyl, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, allyl, cyclohexylmethyl, or phenylmethyl, R³ and R⁶ independently of one another represent hydrogen, ethyl, propyl, isopropyl, butyl, isobutyl, sec-butyl, pentyl, isopentyl, sec-pentyl, hexyl, isohexyl, sec-hexyl, heptyl, isoheptyl, sec-heptyl, octyl, isooctyl, sec-octyl, vinyl, allyl, cyclohexylmethyl, pyridylmethyl, or phenylmethyl, B represents hydroxyl or tert-butoxy or its optical isomer or racemate.

5. The method according to claim 1, wherein the tetradepsipeptide is tert-butyl-N-ethyl-L-leucyl-D-lactyl-N-ethyl-L-leucyl-D-3-phenyllactate.

6. The method according to claim 1, wherein the tetradepsipeptide in N-benzyl-N-propyl-L-leucyl-D-lactyl-N-propyl-L-leucyl-D-phenyllactic acid.

7. The method according to claim 1, wherein the tetradepsipeptide is tert-butyl-N-methyl-L-phenylalanyl-D-lactyl-N-methyl-D-phenylalanyl-D-lactate.

8. The method according to claim 1, wherein the tetradepsipeptide is tert-butyl-N-benzyl-N-methyl-L-leucyl-D-lactyl-N-methyl-L-leucyl-D-3-phenyllactate.

9. A process for the preparation of endoparasiticidal compositions which comprises mixing a compound of the formula

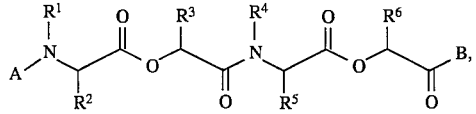

in which

A represents hydrogen, alkyl, aralkyl or an acyl radical of the formula —CO—R⁹, in which R⁹ represents straight-chain or branched alkyl, alkoxy, aralkyl or aralkoxy having up to 6 carbon atoms in the alkyl moiety, R¹ and R⁴ independently of one another represent hydrogen, $C_1$–$C_8$-alkyl, $C_3$–$C_6$-cycloalkyl or aralkyl, R² and R⁵ independently of one another represent hydrogen, straight-chain or branched alkyl having up to 8 carbon atoms, hydroxyalkyl, alkanoyloxyalkyl, alkoxyalkyl, aryloxyalkyl, mercaptoalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, guanidinoalkyl, which itself is optionally substituted by one or two benzyloxycarbonyl radicals or by one, two, three or four alkyl radicals, or represent alkoxycarbonylaminoalkyl, 9-fluorenylmethoxycarbonyl-(FMOC)aminoalkyl, alkenyl, cycloalkyl, cycloalkylalkyl and optionally substituted aryl, optionally substituted arylalkyl or optionally substituted hetarylmethyl, wherein the substituents are halogen, hydroxyl, alkyl, alkoxy, nitro, or a radical —NR¹⁰R¹¹, in which R¹⁰ and R¹¹ independently of one another represent hydrogen or alkyl or R¹⁰ and R¹¹ together with the adjacent N atom represent a carbocyclic 5-, 6-, 7- or 8-membered ring which is optionally interrupted by O, S and N and which is optionally substituted by $C_1$–$C_4$-alkyl, R³ and R⁶ independently of one another represent hydrogen, straight-chain or branched alkyl having up to 8 carbon atoms, hydroxyalkyl, alkanoyloxyalkyl, alkoxyalkyl, aryloxyalkyl, alkylthioalkyl, alkylsulphinylalkyl, alkylsulphonylalkyl, carboxyalkyl, alkoxycarbonylalkyl, arylalkoxycarbonylalkyl, carbamoylalkyl, aminoalkyl, alkylaminoalkyl, dialkylaminoalkyl, alkoxycarbonylaminoalkyl, alkenyl, cycloalkyl, cycloalkylalkyl and optionally substituted aryl, optionally substituted arylalkyl or optionally substituted hetarylmethyl, wherein the substituents are halogen, hydroxyl, alkyl, alkoxy, nitro, or a radical —NR¹⁰—R¹¹, in which R¹⁰ and R¹¹ independently of one another represent hydrogen or alkyl or R¹⁰ and R¹¹ together with the adjacent N atom represent a carbocyclic 5-, 6-, 7- or 8-membered ring which is optionally interrupted by O, S and N and which is optionally substituted by $C_1$–$C_4$-alkyl, B represents hydroxyl, alkoxy having up to 4 carbon atoms or the radical NR⁷R⁸, in which R⁷ and R⁸ represent hydrogen, alkyl, aralkyl or aryl, with an extender and/or a surfactant.

10. The method according to claim 1, wherein

A represents hydrogen or $C_{1-6}$-alkyl or benzyl, or represents a group of the formula —CO—R⁹, in which R⁹ represents straight-chain or branched $C_{1-4}$-alkyl, $C_{2-4}$-alkenyl, $C_{1-4}$-alkoxy or phenyl-alkoxy having up to 6 carbon atoms in the alkyl moiety, R¹ and R⁴ independently of one another represent hydrogen, $C_{1-6}$-alkyl, $C_{3-6}$-cycloalkyl, or phenyl-$C_{1-4}$-alkyl, R² and R⁵ independently of one another represent hydrogen methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, octyl, isooctyl, sec-octyl, hydroxymethyl, 1-hydroxyethyl, acetoxymethyl, 1-acetoxyethyl, 1-methoxyethyl, benzyloxymethyl, 1-benzyl-oxyethyl, mercaptomethyl, methylthioethyl, methylsulphinylethyl, methylsulphonylethyl, carboxymethyl, carboxyethyl, methoxycarbonylmethyl, ethoxycarbonylethyl, benzyloxycarbonylmethyl, carbamoylmethyl, carbamoylethyl, aminopropyl, aminobutyl, methylaminopropyl, methylaminobutyl, dimethylaminopropyl, dimethylaminobutyl, guanidopropyl, tertbutoxycarbonylaminopropyl, tert-butoxycarbonylaminobutyl, 9-fluorenylmethoxy-carbonyl(Fmoc)aminopropyl, 9-fluorenylmethoxy-carbonyl(Fmoc)aminobutyl, vinyl, allyl, butenyl, cyclopentyl, cyclohexyl, cycloheptyl, cyclopentylmethyl, cyclohexylmethyl, cycloheptylmethyl, aryl, phenyl-$C_2$–$C_4$-alkyl which is optionally substituted by radicals selected from the group consisting of fluorine, chlorine, bromine, iodine, hydroxyl, methoxy, ethoxy, methyl, nitro and a radical —$NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which is optionally substituted by $C_1$–$C_4$-alkyl, or $R^2$ and $R^5$ independently represent benzothien-2-yl-methyl, benzothien-3-yl-methyl, naphth-1-yl-methyl, naphth-2-yl-methyl, pyrid-2-yl-methyl, pyrid-3-yl-methyl, fur-2-yl-methyl, fur-3-yl-methyl, indol-3-yl-methyl, N-methyl-indol-3-yl-methyl, imidazol-4-yl-methyl, or N-methyl-imidazol-4-yl-methyl, $R^3$ and $R^6$ independently of one another represent hydrogen, methyl, ethyl, propyl, isopropyl, butyl, isobutyl, sec-butyl, tert-butyl, pentyl, isopentyl, sec-pentyl, hexyl, isohexyl, sec-hexyl, heptyl, isoheptyl, sec-heptyl, tert-heptyl, octyl, isooctyl, sec-octyl, hydroxymethyl, 1-hydroxyethyl, methoxymethyl, 1-methoxyethyl, $C_1$–$C_4$-alkanoyloxy-$C_2$–$C_6$-alkyl, benzyloxymethyl, 1-benzyloxyethyl, mercaptomethyl, methylthioethyl, methylsulphinylethyl, methylsulphonylethyl, carboxymethyl, carboxyethyl, methoxycarbonylmethyl, ethoxycarbonylethyl, benzyloxycarbonylmethyl, carbamoylmethyl, carbamoylethyl, aminopropyl, aminobutyl, methylaminopropyl, methylaminobutyl, dimethylaminopropyl, dimethylaminobutyl, vinyl, allyl, butenyl, cyclopentyl, cyclohexyl, cycloheptyl, cyclopentylmethyl, cyclohexylmethyl, cycloheptylmethyl, aryl, phenyl-$C_1$–$C_4$-alkyl, which is optionally substituted by radicals selected from the group consisting of fluorine, chlorine, bromine, iodine, hydroxyl, methoxy, ethoxy, methyl, nitro and a radical —$NR^{10}R^{11}$, in which $R^{10}$ and $R^{11}$ independently of one another represent hydrogen or alkyl or $R^{10}$ and $R^{11}$ together with the adjacent N atom represent a carbocyclic 5-, 6-, 7- or 8-membered ring which is optionally substituted by $C_1$–$C_4$-alkyl, or $R^3$ and $R^6$ independently represent benzothien-2-yl-methyl, benzothien-3-yl-methyl, naphth-1-yl-methyl, naphth-2-yl-methyl, pyrid-2-yl-methyl, pyrid-3-yl-methyl, fur-2-yl-methyl, fur-3-yl-methyl, indol-3-yl-methyl, N-methyl-indol-3-yl-methyl, imidazol-4-yl-methyl, or N-methyl-imidazol-4-yl-methyl, B represents hydroxyl, tert-butoxy or the radical $NR^7R^8$, in which $R^7$ and $R^8$ independently of one another represent hydrogen, methyl, ethyl, isopropyl, tert-butyl, benzyl, cyclopropyl, cyclohexyl, or phenyl, or its optical isomer or racemate.

* * * * *

UNITED STATES PATENT AND TRADEMARK OFFICE
CERTIFICATE OF CORRECTION

PATENT NO. : 5,571,793
DATED : November 5, 1996
INVENTOR(S) : Scherkenbeck, et al.

It is certified that error appears in the above-indentified patent and that said Letters Patent is hereby corrected as shown below:

Col. 22, line 4     After " $R^5$ " delete " or "

Col. 24, claim 10 line 2     Delete " $C_{1-6}$-alkyl " and substitute -- $C_{1-4}$-alkyl --

Signed and Sealed this

First Day of July, 1997

Attest:

BRUCE LEHMAN

*Attesting Officer*     *Commissioner of Patents and Trademarks*